(12) United States Patent
Kondo et al.

(10) Patent No.: US 8,286,793 B2
(45) Date of Patent: *Oct. 16, 2012

(54) INDIVIDUAL PACKAGE OF TAMPON

(75) Inventors: Hideki Kondo, Kagawa (JP); Akie Kikuchi, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 142 days.

This patent is subject to a terminal disclaimer.

(21) Appl. No.: 12/595,157

(22) PCT Filed: Nov. 4, 2008

(86) PCT No.: PCT/JP2008/057156
§ 371 (c)(1),
(2), (4) Date: Oct. 8, 2009

(87) PCT Pub. No.: WO2008/133039
PCT Pub. Date: Nov. 6, 2008

(65) Prior Publication Data
US 2010/0042064 A1    Feb. 18, 2010

(30) Foreign Application Priority Data

Apr. 13, 2007 (JP) ................................. 2007-106556

(51) Int. Cl.
*B65D 33/00* (2006.01)
*A61F 13/551* (2006.01)
(52) U.S. Cl. .... 206/440; 206/438; 206/484; 604/385.02
(58) Field of Classification Search .................. 206/440, 206/438, 484; 604/385.02, 358; 383/200, 383/207, 209; 229/87.03
See application file for complete search history.

(56) References Cited

U.S. PATENT DOCUMENTS
4,373,631 A    2/1983  Friese
(Continued)

FOREIGN PATENT DOCUMENTS
EP    1304096 A2    4/2003
(Continued)

OTHER PUBLICATIONS
International Search Report from corresponding PCT application No. PCT/JP2008/057156 dated Jul. 15, 2008, 4 pages.
(Continued)

*Primary Examiner* — Steven A. Reynolds
(74) *Attorney, Agent, or Firm* — Brinks Hofer Gilson & Lione

(57) ABSTRACT

An individual package of tampon that has a bag body capable of easily accommodating an applicator after use. The individual package of tampon comprises a vertically long, flat bag body (2) consisting of a sheet member and, individually enclosed therein, a tampon with applicator. The bag body (2) has a first face (21) and a second face (22); a first side junction area (23) and second side junction area (24) joining the first face (21) and second face (22) together at both sides in the width direction thereof; a bottom junction area (26) provided so as to tie the first side junction area (23) and second side junction area (24) together at a bottom portion (25) being one of the edges in the longitudinal direction thereof; and a slack area (28) provided on the first face (21) and/or second face (22) so that the length between the first side junction area (23) and second side junction area (24) on the first face (21) and/or second face (22) is longer than the distance between the first side junction area (23) and second side junction area (24).

8 Claims, 8 Drawing Sheets

U.S. PATENT DOCUMENTS

| | | | | |
|---|---|---|---|---|
| 4,735,316 | A * | 4/1988 | Froidh et al. | 206/438 |
| 4,881,644 | A * | 11/1989 | Norquest et al. | 206/363 |
| 5,133,457 | A * | 7/1992 | Kadel | 206/438 |
| 5,580,625 | A * | 12/1996 | Capy et al. | 428/35.2 |
| 5,743,460 | A * | 4/1998 | Capy et al. | 229/87.03 |
| 5,986,165 | A * | 11/1999 | Moder et al. | 604/358 |
| 6,082,898 | A * | 7/2000 | Capy et al. | 383/87 |
| 6,276,529 | B1 * | 8/2001 | Feehan, Jr. | 206/469 |
| 6,299,607 | B1 | 10/2001 | Osborn | |
| 6,773,421 | B2 * | 8/2004 | Bosselaar et al. | 604/385.02 |
| 6,994,696 | B2 * | 2/2006 | Suga | 604/385.02 |
| 2003/0065300 | A1 * | 4/2003 | Suga | 604/385.02 |
| 2004/0112779 | A1 * | 6/2004 | Arndt | 206/363 |
| 2006/0212015 | A1 * | 9/2006 | Peele | 604/385.13 |
| 2007/0151885 | A1 * | 7/2007 | Loyd et al. | 206/440 |
| 2007/0156109 | A1 * | 7/2007 | Loyd et al. | 604/385.02 |

FOREIGN PATENT DOCUMENTS

| | | |
|---|---|---|
| EP | 2008628 A1 | 12/2008 |
| EP | 2135592 A1 | 12/2008 |
| JP | 45-003200 U | 2/1970 |
| JP | 46-031839 U | 11/1971 |
| JP | 55-143149 | 11/1980 |
| JP | S62-18128 U | 2/1987 |
| JP | 2001-523521 | 11/2001 |
| JP | 2003-116914 | 4/2003 |
| JP | 2004-097251 | 4/2004 |
| JP | 2006-167407 | 6/2006 |
| JP | 2007-054087 | 3/2007 |
| JP | 2007-282918 | 11/2007 |
| JP | 2008-259583 | 10/2008 |
| JP | 2008-259773 | 10/2008 |
| WO | WO 2007/075217 A1 | 7/2007 |

OTHER PUBLICATIONS

European Search Report issued in corresponding EP application No. 08740253.3, mailed Jan. 4, 2012, 3 pages.

* cited by examiner

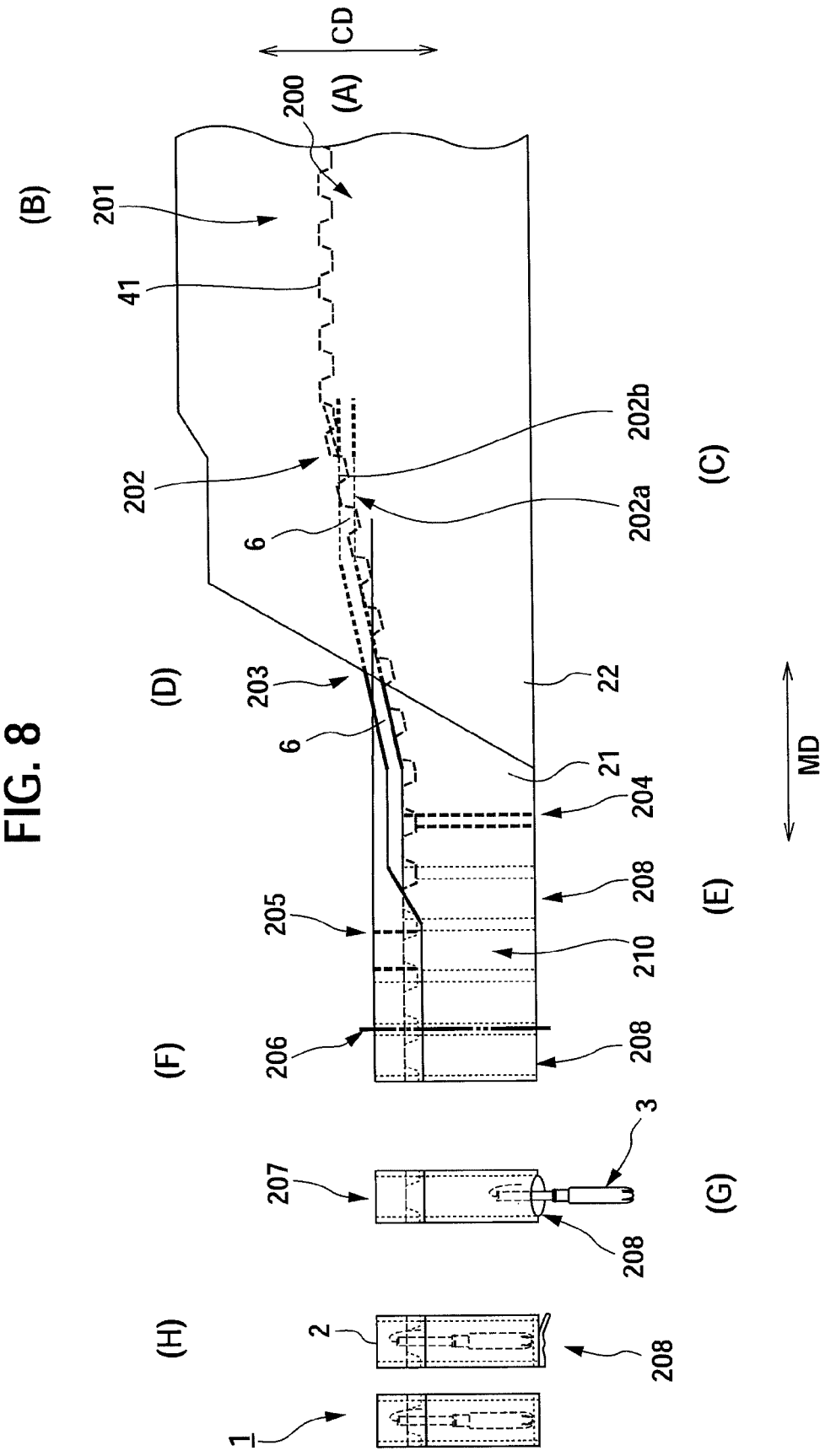

INDIVIDUAL PACKAGE OF TAMPON

RELATED APPLICATIONS

The present application is a 35 U.S.C. §371 national stage filing of International Patent Application No. PCT/JP2008/057156, filed Apr. 11, 2008, to which priority is claimed under 35 U.S.C. §120 and through which priority is claimed under 35 U.S.C. §119 to Japanese Priority Patent Application No. 2007-106556, filed Apr. 13, 2007.

TECHNICAL FIELD

The present invention relates to an individual packaging body of tampon.

BACKGROUND ART

Conventionally, as an absorbent article used by inserting into a vaginal cavity of a menstruating woman, a so-called sanitary tampon (also referred to as tampon hereinafter) provided with a cylindrical absorbent core for absorbing a body fluid and the like and a string attached at an end of the absorbent core has been widely known. Such a tampon is generally housed inside an applicator that is an insertion aid for a tampon, and the absorbent core thereof is inserted into the body using the applicator. For example, in a case of a tampon with an applicator, an applicator that houses an absorbent core is inserted to a predetermined position in a vaginal cavity and the absorbent core is pushed out from the applicator, thereby enabling more reliable insertion of the absorbent core deep into the vaginal cavity. In addition, since the tampon is required to be stored in a clean manner until use, an individual packaging body in which the tampon is individually packed in a bag body slightly larger than the tampon is available in the market.

As such an individual packaging body of a tampon, the applicant has previously proposed an individual packaging body of a tampon including a tampon with an applicator and a bag body for individually packing the tampon in which a perforated line for tearing is provided at a predetermined position of the bag body (see Japanese Unexamined Utility Model Application Publication No. S62-18128, hereinafter referred to as Patent Document 1). According to the individual packaging body of a tampon disclosed in Patent Document 1, since the bag body can be easily opened when used at the predetermined position in which the perforated line is provided, chance for a user's hand to directly contact the tampon can be reduced by accordingly adjusting the position of the multi perforated line, thereby allowing sanitary use of the tampon.

DISCLOSURE OF THE INVENTION

Problems to be Solved by the Invention

Meanwhile, a user of the tampon with an applicator often discards the applicator soiled with body fluid such as menstrual blood after inserting the tampon in a state of being housed in the bag body that was used to pack the tampon, in order to avoid the body fluid from soiling a hand and the like.

However, it has been difficult to insert the used applicator soiled with body fluid into the bag body and a torn opening of the bag body could be easily soiled when inserting the used applicator. In the individual packaging body of a tampon disclosed in Patent Document 1, there is no particular device for facilitating inserting the used applicator into the bag body.

Given this, the present invention aims at providing an individual packaging body of a tampon including a bag body allowing easy housing of a used applicator.

Means for Solving the Problems

The present inventors found that the abovementioned problem could be solved by using a bag body of a predetermined configuration for an individual packaging body of a tampon, thereby leading to the completion of the present invention. More specifically, the present invention provides the following.

In a first aspect of the present invention, an individual packaging body of a tampon includes an elongated and flat bag body configured with a sheet-like member and a tampon with an applicator that is to be individually packed in the bag body. The bag body includes: a first face and a second face that configure the bag body and are disposed so as to face each other; a first lateral joint portion and a second lateral joint portion that join the first face and the second face on both sides in a width direction; a bottom joint portion that is formed in a bottom portion, which is a first end portion in a longitudinal direction, so as to connect the first lateral joint portion and the second lateral joint portion, and joins the first face and the second face; a slack portion that is formed on at least any one of the first face and the second face, and configured so that a length thereof between the first lateral joint portion and the second lateral joint portion on the at least any one of the first face and the second face is greater than a distance between the first lateral joint portion and the second lateral joint portion.

According to a second aspect of the present invention, in the individual packaging body of a tampon as described in the first aspect, the slack portion slackens more greatly on a side of the bottom joint portion than in an upper end portion, which is an end portion opposite to the bottom portion of the bag body in the longitudinal direction.

According to a third aspect of the present invention, in the individual packaging body of a tampon as described in the first or the second aspect, the slack portion is formed dominantly on a side of the bottom joint portion.

According to a fourth aspect of the present invention, in the individual packaging body of a tampon as described in any one of the first to the third aspects, the bag body includes: a tearing portion having at least one slit portion that is formed continuously or intermittently so as to extend in a width direction of the bag body, at a position a predetermined distance away from the upper end portion of the first face; and a flap portion that can be opened by a force in a longitudinal direction of the bag body.

According to a fifth aspect of the present invention, in the individual packaging body of a tampon as described in the fourth aspect, the bag body is configured so that, in an open state, a length in the longitudinal direction of the second face is greater than a length in the longitudinal direction of the first face.

Here, the length in the longitudinal direction of the second face in an open state is a length from the bottom portion to the upper end portion in the longitudinal direction of the second face of the bag body in an open state. In addition, the length in the longitudinal direction of the first face in an open state is a length from the bottom portion to the tearing portion in the longitudinal direction of the first face of the bag body in an open state.

According to a sixth aspect of the present invention, in the individual packaging body of a tampon as described in the fourth or the fifth aspect, a distance in the bag body between the first lateral joint portion and the second lateral joint portion in the tearing portion is greater than a distance between the first lateral joint portion and the second lateral joint portion in the bottom portion.

According to a seventh aspect of the individual packaging body of a tampon as described in any one of the fourth to the sixth aspects, the flap portion includes a grip portion integrally formed with the flap portion.

According to an eighth aspect of the present invention, in the individual packaging body of a tampon as described in any one of the first to the seventh aspects, the sheet-like member is configured with a film material, and the first lateral joint portion, the second lateral joint portion, and the bottom joint portion are joined by heat sealing.

According to a ninth aspect of the present invention, in the individual packaging body of a tampon as described in any one of the first to the eighth aspects, a distance in the bag body between the first lateral joint portion and the second lateral joint portion is in a range of 10 to 40 mm.

In a tenth aspect of the present invention, a manufacturing method for the individual packaging body of a tampon as described in any one of the first to the ninth aspects includes: an unreeling step of unreeling a strip-shaped sheet-like member from a raw fabric; a folding step of folding the strip-shaped sheet-like member that is unreeled so that both end portions in a CD direction, which is orthogonal to an MD direction that is a flow direction of the strip-shaped sheet-like member, overlap each other; a bag body continuous body forming step of forming a bag body continuous body having an one end in the CD direction being an open end, by way of joining by heat sealing extending in the CD direction, at predetermined intervals in the MD direction, in a state that the folded strip-shaped sheet-like member is extended in the MD direction an insertion step of inserting the tampon into the bag body continuous body from the open end; and a joining step of joining the open end by heat sealing.

In an eleventh aspect of the present invention, an individual packaging body of a tampon includes an elongated and flat bag body configured with a sheet-like member and a tampon with an applicator that is to be individually packed in the bag body. The bag body includes: a first face and a second face that configure the bag body and are disposed so as to face each other; a first lateral joint portion and a second lateral joint portion that join the first face and the second face on both sides in a width direction; and a bottom joint portion that is formed in a bottom portion, which is a first end portion in a longitudinal direction, so as to connect the first lateral joint portion and the second lateral joint portion, and joins the first face and the second face, and, in a case where the bag body is in a natural state, the first face and the second face each have a non-flat portion and in the non-flat portion, the first surface and the second surface are spaced away from each other and a gap is formed between the first face and the second face.

Effects of the Invention

According to the present invention, an individual packaging body of a tampon including a bag body allowing easy housing of a used applicator can be provided. In addition, according to the manufacturing method of the present invention, the individual packaging body of a tampon of the present invention can be easily manufactured.

BRIEF DESCRIPTION OF THE DRAWINGS

FIG. 8 is a schematic view illustrating a manufacturing method of the individual packaging body of a tampon of the present embodiment.

EXPLANATION OF REFERENCE NUMERALS

Figure 1:
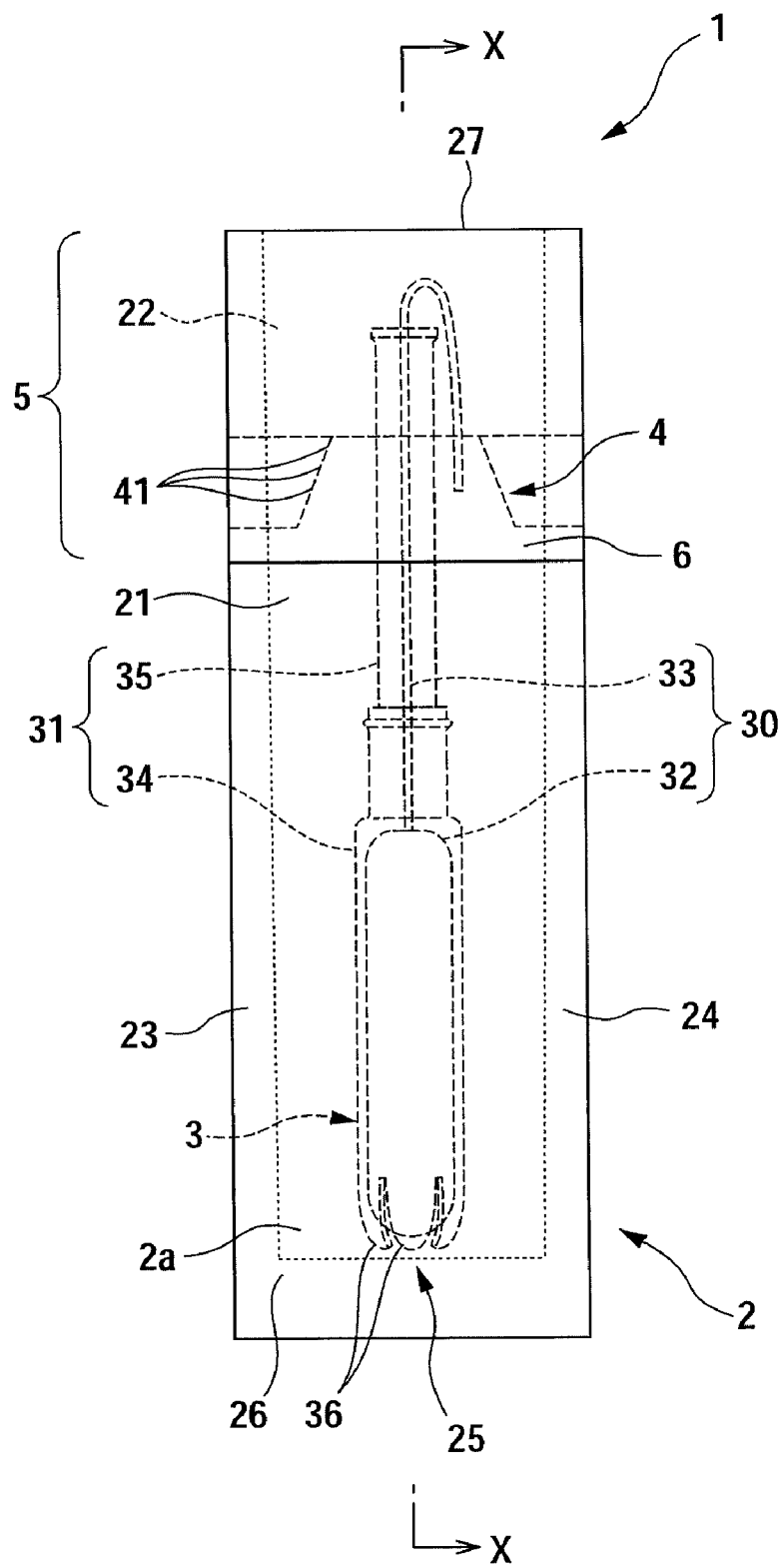
FIG. 1 is a front view illustrating an embodiment of the individual packaging body of a tampon of the present invention.

1 Individual packaging body of a tampon
2 Bag body
21 First face
22 Second face
23 First lateral joint portion
24 Second lateral joint portion
25 Bottom portion
26 Bottom joint portion
27 Folded end
28 Slack portion
3 Tampon with an applicator
30 Tampon main body
31 Applicator
32 Absorbent core
33 String
34 Outer cylinder
35 Inner cylinder
36 Petal
4 Tearing portion
41 Slit portion
5 Flap portion
51 Lower end portion
52 Peak portion
53 Valley portion
6 Grip portion

PREFERRED MODE FOR CARRYING OUT THE INVENTION

The present invention is described hereinafter based on a preferred embodiment, with reference to the drawings.

Figure 2:
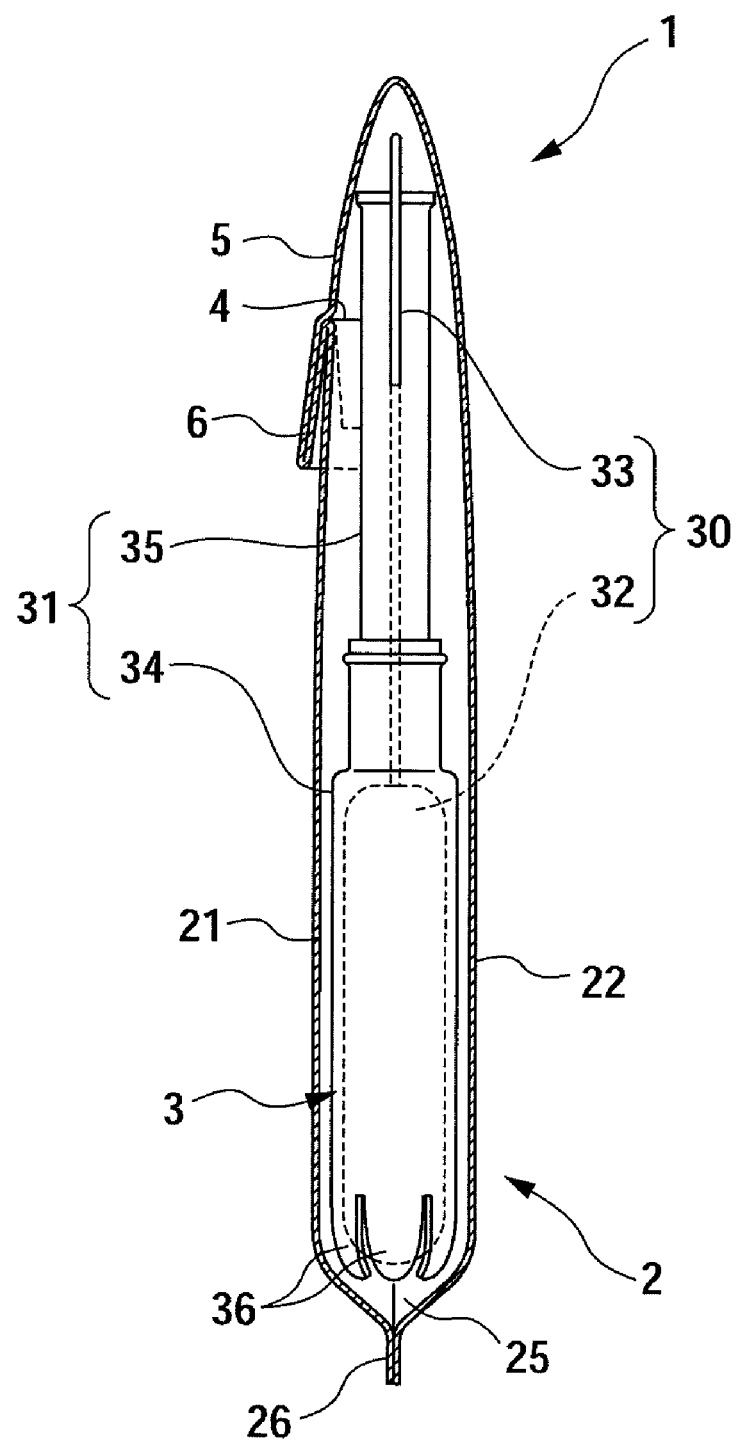
FIG. 2 is a sectional view taken along the line X-X of FIG. 1.
Figure 5:
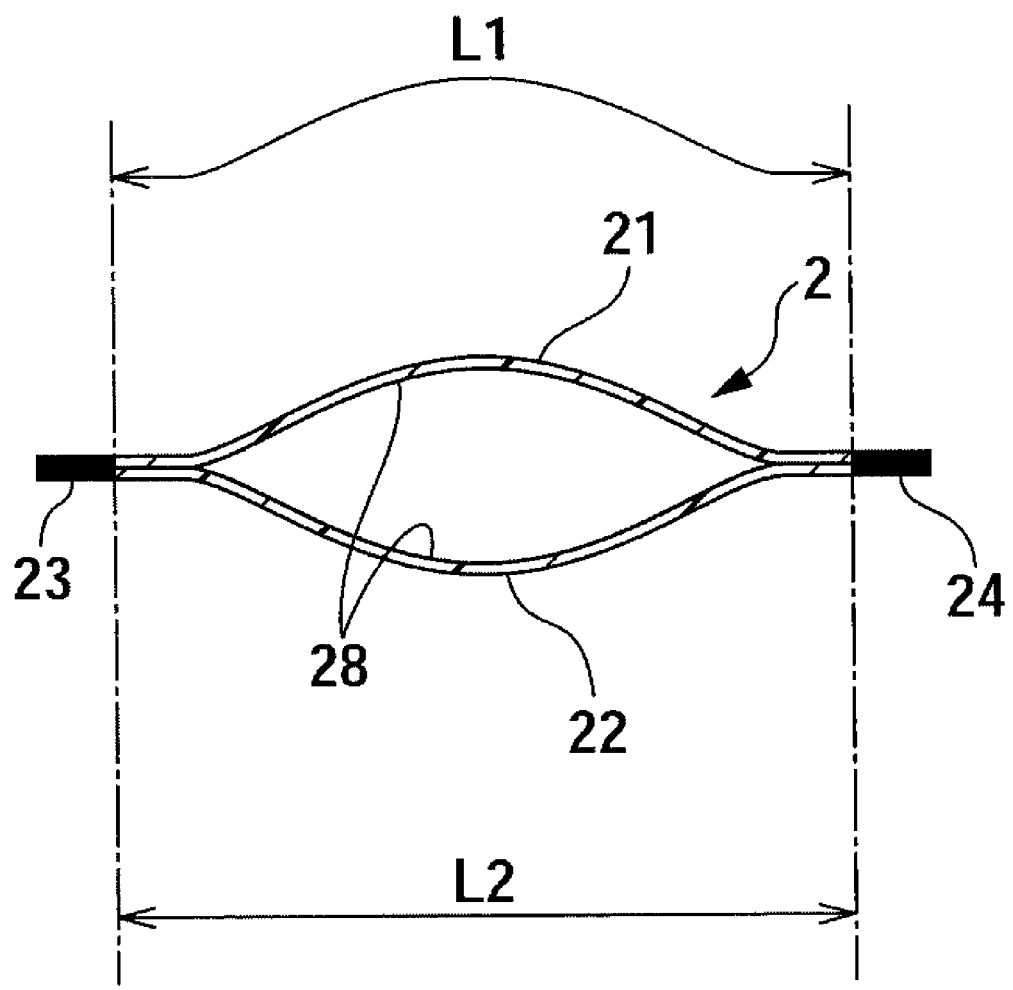
FIG. 5 is a sectional view taken along the line Y-Y of FIG. 3.

As shown in FIGS. 1 and 2, an individual packaging body of a tampon 1 of the present embodiment includes an elongated and flat bag body 2 configured with a sheet-like member and a tampon with an applicator 3 that is to be individually packed in the bag body 2. It should be noted that "flat" indicates a substantially planar state, and the flat bag body 2 has, more specifically, a state where a tampon is not packed therein and a distance between a first face 21 and a second face 22 composing the bag body 2 is smaller than a width of the bag body 2 as shown in FIG. 5. In other words, the bag body 2 is small in thickness.

The tampon with an applicator 3 includes, as shown in FIG. 1, a tampon main body 30 including an absorbent core 32 and a string 33 extending from the rear end portion of the absorbent core 32, and an applicator 31 for housing the tampon main body 30.

The tampon main body 30 is formed by compressing a sheet-like absorbent core 32, in which the string 33 is sewn onto a face thereof, into a cylindrical shape. For example, a hydrophilic fiber such as cotton and rayon with a liquid permeable sheet such as a nonwoven fabric covering a surface thereof can be used as the absorbent core 32. The absorbent core 32, which is formed in a cylindrical shape, absorbs body fluid such as menstrual blood and swells when being inserted into the vaginal cavity of a woman during menstruation. While the absorbent core 32 is inserted into the vaginal cavity, the string 33 is kept out of the vaginal cavity, and then, the used absorbent core 32 can be removed from the vaginal cavity by pulling this string 33.

The applicator 31 is made of a synthetic resin material, and as shown in FIG. 1, has an outer cylinder 34 having the absorbent core 32 housed therein and an inner cylinder 35 which is slidably inserted in the outer cylinder 34 from the rear end portion of the absorbent core 32. In an apex portion of the outer cylinder 34, a plurality of petals 36, which are separated from each other, is integrally formed. The string 33 extending from the rear end portion of the absorbent core 32 is inserted in the inner cylinder 35 and projects backward from a rear end portion of the inner cylinder 35. The tampon with an applicator 3 is used in a state where the outer cylinder 34 of the applicator 31 is inserted into the vaginal cavity and the inner cylinder 35 is pushed into the outer cylinder 34. Here, the absorbent core 32 in the outer cylinder 34 is moved by the inner cylinder 35 toward the apex of the external cylinder 34. Thereafter, the absorbent core 32 thus moved deforms the petals 36 in the apex portion of the outer cylinder 34 to open, and is pushed out from the external cylinder 34 and inserted into the vagina.

Figure 3:
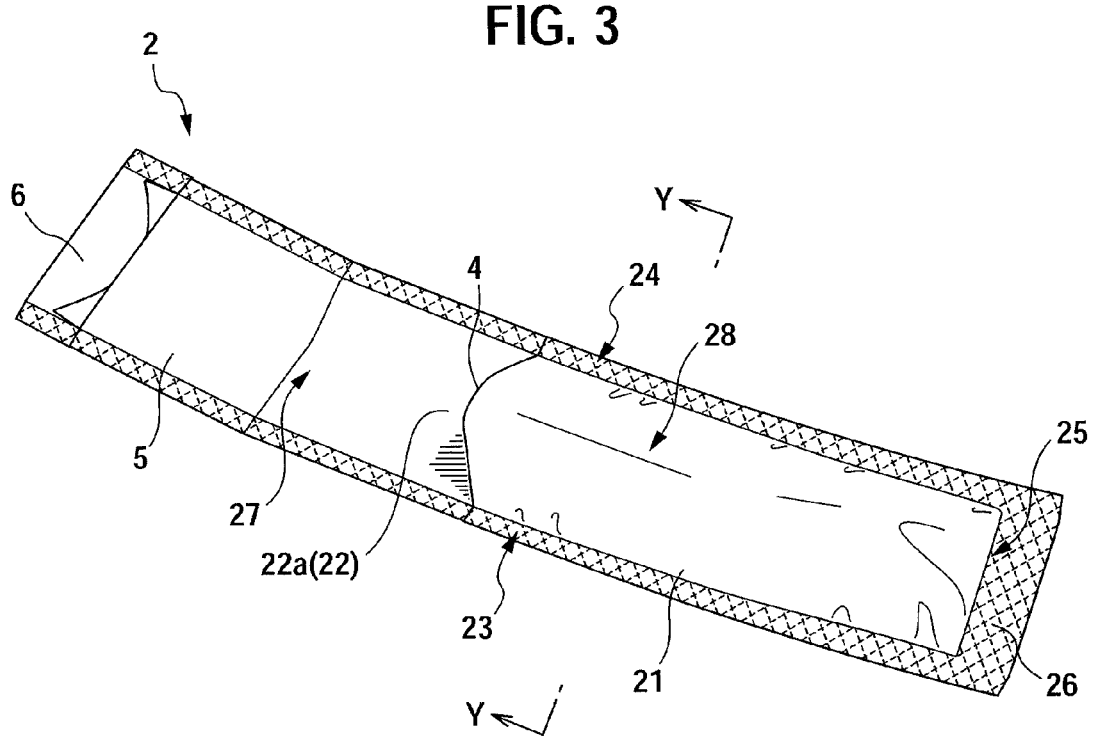
FIG. 3 is a perspective view illustrating an open state of a bag body of the individual packaging body of a tampon shown in FIG. 1.
Figure 4:
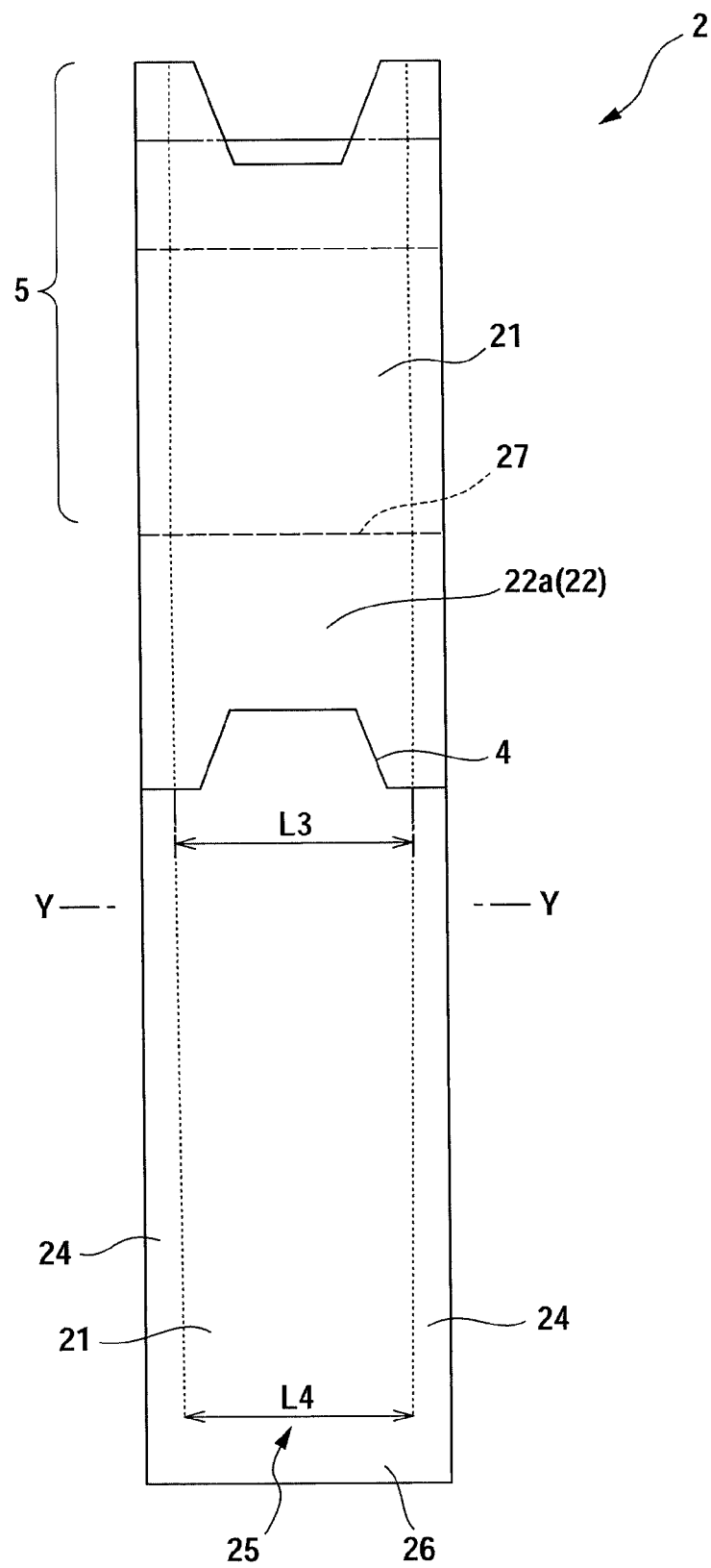
FIG. 4 is a front view illustrating an open state of a bag body of the individual packaging body of a tampon shown in FIG. 1.

As shown in FIGS. 3 to 5, the bag body 2 has a vertically long, substantially rectangular shape in a planar view and includes the first face 21 and the second face 22 that are disposed so as to face each other. In the bag body 2, the first face 21 and the second face 22 are joined on both sides thereof in a width direction, and forms a first lateral joint portion 23 and a second lateral joint portion 24. In addition, in a bottom portion 25, which is a first end portion in a longitudinal direction thereof, the first face 21 and the second face 22 are joined so as to connect the first lateral joint portion 23 and the second lateral joint portion 24, thereby forming a bottom joint portion 26.

In the present embodiment, the first face 21 and the second face 22 are configured with one piece of a sheet-like member. The bag body 2 is formed by joining the first face 21 and the second face 22, which are formed by folding one piece of the sheet-like member, at the first lateral joint portion 23, the second lateral joint portion 24, and the bottom joint portion 26. In other words, the bag body 2 has, as shown in FIG. 1, both side portions and the bottom portion 25 being joined ends and a second end portion in the longitudinal direction being a folded end 27. A manufacturing method is described later.

The bag body 2 includes, as shown in FIG. 5, a slack portion 28 that is formed so that a length L1 thereof between the first lateral joint portion 23 and the second lateral joint portion 24 on each of the first face 21 and the second face 22 is greater than a distance L2 between the first lateral joint portion 23 and the second lateral joint portion 24.

Here, the length L1 between the first lateral joint portion 23 and the second lateral joint portion 24 on each of the first face 21 and the second face 22 is a length in a width direction of the sheet-like member itself on each of the first face and the second face 22. On the other hand, the distance L2 between the first lateral joint portion 23 and the second lateral joint portion 24 is a linear distance between the first lateral joint portion 23 and the second lateral joint portion 24.

In addition, the slack portion 28 indicates a non-flat portion in which the first face 21 and the second face 22 are not flat in a case where a tampon is not housed in the flat bag body 2, in other words in a natural state. In a cross-section of FIG. 5, the slack portion 28 is a portion in which the first face 21 and the second face 22 are not parallel in a horizontal direction in a natural state.

In the present embodiment, the length L1 between the first lateral joint portion 23 and the second lateral joint portion 24 on each of the first face 21 and the second face 22 is substantially equal to each other and the slack portion 28 is formed on both the first face 21 and the second face 22. In other words, a non-flat portion is formed on each of the first face 21 and the second face 22, in which the first face 21 and the second face 22 are spaced apart from each other, thereby generating a gap between the first face 21 and the second face 22.

As shown in FIG. 5, by providing the slack portion 28 in the flat bag body 2, the first face 21 and the second face 22 in the bag body 2, from which a tampon is taken out for use, do not closely contact each other and are spaced apart from each other, thereby generating a gap therebetween. As described above, by generating a gap between the first face 21 and the second face 22, a cross-section in the width direction of the bag body 2 of the individual packaging body of a tampon 1 in the present embodiment easily forms a substantially oval shape when a used applicator 31 is inserted thereinto (see FIG. 5). Namely, a torn opening formed when the tampon is taken off easily has a substantially oval shape. This facilitates insertion of the used applicator 31 into the bag body 2.

It should be noted that the slack portion 28 can be formed by changing the length L1 between the first lateral joint portion 23 and the second lateral joint portion 24 on the first face 21 from the length L1 between the first lateral joint portion 23 and the second lateral joint portion 24 on the second face 22. In this case, even if the first face 21 and the second face 22 slacken toward the same side, a gap is generated between the first face 21 and the second face 22.

As shown in FIG. 1, the bag body 2 includes a tearing portion 4 having at least one slit portion 41 that is formed continuously or intermittently so as to extend in a width direction, at a position a predetermined distance away from the folded end 27 of the first face 21 and a flap portion 5 that can be opened by a force in a longitudinal direction of the bag body 2. In addition, as shown in FIG. 2, the tearing portion 4 is formed to be continuous with and covered with the flap portion 5. Furthermore, the flap portion 5 is continuous with the second face 22 via the folded end 27 and is not separated from the bag body 2 even after opening thereof. This makes the bag body 2 easy to open and does not give an unnecessary cut piece to discard.

In the present embodiment, the tearing portion 4 is formed by intermittently providing a plurality of the slit portions 41 between the first lateral joint portion 23 and the second lateral joint portion 24 on the first face 21. In addition, regarding a shape thereof, the tearing portion 4 is provided in a central region of the first face 21 so as to extend substantially horizontally in the width direction of the bag body 2, and in both end portions so as to extend obliquely downward. In other words, in the present embodiment, the tearing portion 4 is formed in a mountain shape projecting toward the folded end 27. The flap portion 5 is configured to be openable toward the folded end 27 in the longitudinal direction of the bag body 2.

By thus providing the tearing portion 4 on the first face 21, the stability of the substantially oval shape of the torn opening can be improved.

In addition, by thus forming the tearing portion 4 in a mountain shape as shown in FIG. 4, the first face 21 and the second face 22 can be spaced apart from each other more easily at the tearing portion 4, thereby facilitating insertion of the used applicator 31 thereto. This is because, in a case where the bag body 2 is in an open state, a width of the first face 21 in the vicinity of the tearing portion 4 gradually narrows down as approaching the folded end 27 from the bottom portion 25, as shown in FIG. 4, thereby making the sheet-like member constituting the first face 21 in the vicinity of the tearing portion 4 easier to bend and facilitating forming of the substantially oval shape of the torn opening. Furthermore, an apex portion of the mountain shape of the tearing portion 4 is preferably made flat in order to facilitate opening of the tearing portion 4.

The flap portion 5 includes a grip portion 6 that is formed integrally with the flap portion 5. The grip portion 6 is formed by folding a portion of the sheet-like member constituting the flap portion 5 so as to form a peak portion and a valley portion. More specifically, the grip portion 6 is formed by folding the sheet-like member so as to form: a peak portion 52 at a position on the sheet-like member corresponding to a lower end portion 51 of the flap portion 5; and a valley portion 53 at a predetermined position on the sheet-like member between the lower end portion 51 of the flap portion 5 and the tearing portion 4. By thus providing a grip portion 6 in the flap portion 5, a user can open the flap portion 5 by gripping the grip portion 6, thereby facilitating opening of the bag body 2 at the time of use of the tampon.

In addition, in the grip portion 6 formed by folding the sheet-like member, the sheet-like member has a four-layered structure (the grip portion 6, the first face 21, and the second face 22) as shown in FIG. 2. On the other hand, in a portion other than the grip portion 6, the sheet-like member has a bilayer structure (the first face 21 and the second face 22). Therefore, as described later, in a case where the first lateral joint portion 23 and the second lateral joint portion 24 are formed by heat sealing under uniform conditions, seal strength in the grip portion 6, where there is a plurality of portions that seal a large number of pieces of the sheet-like member being layered, is lower than that in a portion other than the grip portion 6. As a result, heat sealing in the grip portion 6 is easy to peel, thereby facilitating opening of the tearing portion 4 by pinching the grip portion 6.

Figure 6:
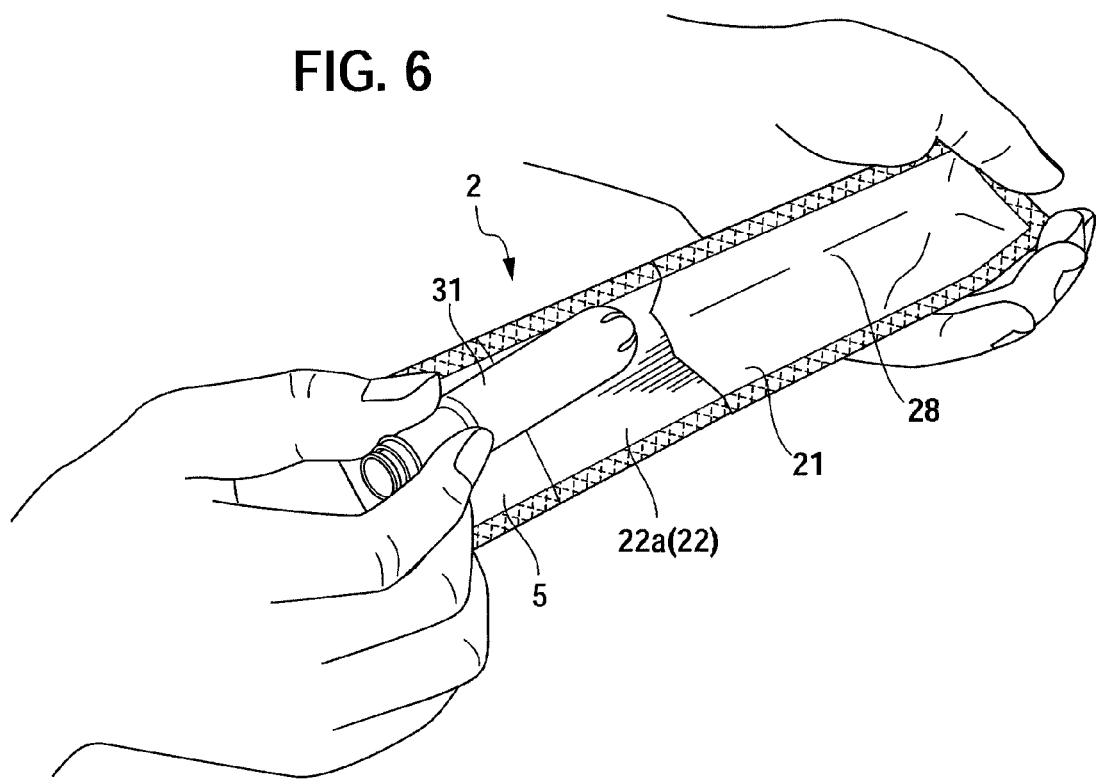
FIG. 6 is a diagram illustrating a used state of the individual packaging body of a tampon of the present embodiment.

As shown in FIG. 4, the bag body 2 is configured so that, in an open state, a length in the longitudinal direction of the second face 22 is greater than a length in the longitudinal direction of the first face 21. By making the length in the longitudinal direction of the second face 22 greater than a length in the longitudinal direction of the first face 21, the bag body 2 being opened has a region 22a where the second face 22 extends to exceed the first face 21 in the longitudinal direction. As shown in FIG. 6, the second face 22 including the region 22a can easily form a shape bending to project toward an opposite side to the first face 21 in a case where the used applicator 31 is inserted into the bag body 2. Therefore, the region 22a extending to exceed the first face 21 acts as a guide portion for insertion, thereby facilitating insertion of the applicator 31 into the bag body 2.

In the present embodiment, the bag body 2 is configured so that a distance L3 between the first lateral joint portion 23 and the second lateral joint portion 24 in the tearing portion 4 (see FIG. 4) is slightly greater than a distance L4 between the first lateral joint portion 23 and the second lateral joint portion 24 in the bottom portion 25 (see FIG. 4). In such a configuration, the slack portion 28 is formed in the bag body 2 in the present embodiment, and slackening (difference between L1 and L2) is greater on a side to the bottom portion 25 than on a side to the tearing portion 4.

In the slack portion 28, a side to the first end in the longitudinal direction of the bag body 2, in other words a side to the bottom joint portion 26, slackens more greatly than a side to the folded end 27. By slackening the slack portion 28 more on the side to the bottom joint portion 26 than on the side to the folded end 27, the gap between the first face 21 and the second face 22 can be stably generated. In addition, the slack portion 28 is formed dominantly on the side to the bottom joint portion 27.

In the present embodiment, the sheet-like member is configured with a film material. In addition, the first lateral joint portion 23, the second lateral joint portion 24, and the bottom joint portion 26 are joined by heat sealing. By thus constituting the sheet-like member of the film material and joining the first lateral joint portion 23, the second lateral joint portion 24, and the bottom joint portion 26 by heat sealing, the slack portion 28 is formed in the bag body 2 in the present embodiment. By thus forming the slack portion 28, a substantially oval shape of a cross-section thereof in the width direction can be stably formed. The slack portion 28 can be formed as follows.

Heat sealing joining is performed by sandwiching the first surface 21 and the second surface 22 by two rotary metal rolls that are heated. Here, in the first lateral joint portion 23, the second lateral joint portion 24, and the bottom joint portion 26 that directly contact the metal rolls, the film material heat-shrinks. In other words, in the first lateral joint portion 23 and the second lateral joint portion 24, a shrinking force in the longitudinal direction is applied to the bag body 2. Meanwhile, in the bottom joint portion 26, a shrinking force in the width direction is applied to the bag body 2. In addition, in the vicinity of the joint portions 23, 24, and 26, the film material slightly expands in a state of being easy to soften due to radiant heat from the metal rolls. The film material expanded by the radiant heat reshrinks when there is no influence of the radiant heat. Shrinkage thereof is greater on an outer face of the first face 21 and the second face 22, which is heavily affected by the radiant heat. As a result, an outward warping force is applied to the first face 21 and the second face 22 due to a shrinking force of the film material in the vicinity of the joint portions 23, 24 and 26.

As described above, due to a shrinking force in the first lateral joint portion 23 and the second lateral joint portion 24 in the longitudinal direction of the bag body 2 and an outward warping force of the first face 21 and the second face 22 in the vicinity of the joint portions 23, 24 and 26, the slack portion 28 is formed in the first face 21 and the second face 22. In addition, a shape of the bag body 2, in which the first face 21 and the second face 22 are spaced apart from each other, is easy to form since the warping force of the first face 21 and the second face 22 is integrated in the lateral joint portions 23 and 24 in both ends and maintained by counteraction. In addition, even if the bag body 2 deforms by being crushed or the like, the oval shape can be easily restored.

It should be noted that, by forming the first lateral joint portion 23 and the second lateral joint portion 24 by heat sealing the film material, which is the sheet-shaped material constituting the first face 21 and the second face 22, in a state of being expanded in the width direction of the bag body 2, the slack portion can be formed more easily. This is because shrinkage of the film material, due to release of the film material from an expanded state after forming the first lateral joint portion 23 and the second lateral joint portion 24, also contributes to forming of the slack portion 28.

In addition, by thus joining the bottom joint portion 26 by heat sealing, the bottom joint portion 26 heat-shrinks in the width direction of the bag body 2. As a result, the distance L4 between the first lateral joint portion 23 and the second lateral joint portion 24 in the bottom portion 25 is smaller than the distance L3 between the first lateral joint portion 23 and the second lateral joint portion 24 in the tearing portion 4 that is not joined by heat sealing, thereby contributing to the formation of the slack portion 28 in the bag body 2.

As the film material used as the sheet-shaped member, a film made of high-density polyethylene (HDPE), low-density polyethylene (LDPE), linear low-density polyethylene (LLDPE), and a combination thereof can be exemplified.

In addition, since the bag body 2 in the present invention is provided with the slack portion 28 and has a structure allowing the substantially oval shape to be easily formed, the bag body 2 facilitating insertion of the used applicator 31 can be manufactured even by using a soft film material that is low in stiffness. Hence, since the individual packaging body of a tampon 1 that does not make a so-called rustling sound, which is made by deformation of a high-stiffness film material, can be provided, it is possible to change a tampon without the fact that the user is menstruating being recognized by another person.

As the soft film material, a polyethylene resin based soft type film having a heat sealing property can be exemplified. The basis weight of the film material is preferably in a range of 20 to 35 g/m$^2$. In addition, these can be of a single layered structure or a multi-layered structure made of a single resin or a plurality of resins.

It should be noted that the sheet-like member is not limited to the abovementioned film materials, and can be, for example, a film made of a thermoplastic resin such as polypropylene (PP), EVA resin (EVA), PET resin (PET), and polyvinyl chloride resin (PVC), a biodegradable film, a nonwoven fabric, and Japanese paper, which may be used singly or in combination. As a combination thereof, a laminated film can be preferably used. As the laminated film, a spun-bonded nonwoven fabric, an SMS (spun-bonded/melt-blown/spun-bonded) nonwoven fabric with laminate-coating on one side thereof, and a laminated body obtained by laminating and joining by an adhesive a nonwoven fabric to a polyethylene film can be preferably used.

In addition, a large number of concavities and convexities is preferably formed on a face of the sheet-like member that is to be an inner face of the bag body 2, by performing an embossing process. As the embossing process, for example, after film forming, the film can be shaped by embossing rolls on which circle patterns are zigzag-aligned, to obtain a pattern height of 90 μm after the embossing process for film shaping. In addition, in the embossing process, the thickness of the sheet-like member after the embossing process is preferably in the range of 0.03 mm to 0.15 mm in order to maintain the strength of the sheet-like member.

In a heat sealing process, sealing temperature is preferably in a range of 80 to 110° C. and pressure is preferably in a range of 15 to 30 kgf/cm. In addition, a heat sealing process having embossed pattern is preferably performed.

As an embossed shape thereof, a square, a rectangle, a diamond shape, a circle and the like can be exemplified. As the embossed pattern, a zigzag pattern can be exemplified.

A preferred size of each of the members constituting the individual packaging body of a tampon 1 according to the present invention is described hereinafter.

The length of the bag body 2 in the longitudinal direction is preferably a length obtained by adding 10 to 40 mm to a total length of the applicator 31, for example. More specifically, regarding a long applicator and a compact applicator suitable for carrying, the following can be exemplified. In a case of a long applicator, with a light type tampon (manufactured by Uni-Charm Corporation) having the applicator 31 of 145 mm in total length, the length in the longitudinal direction of the bag body 2 is preferably in a range of 155 mm to 185 mm. With a regular type tampon (manufactured by Uni-Charm Corporation) having an applicator 31 of 116.5 mm in total length, the length in the longitudinal direction of the bag body 2 is preferably in a range of 127 mm to 157 mm. With a super type tampon (manufactured by Uni-Charm Corporation) having the applicator 31 of 119.5 mm in total length, the length in the longitudinal direction of the bag body 2 is preferably in a range of 130 mm to 160 mm. With other products having the applicator 31 of 126 mm in total length, the length in the longitudinal direction of the bag body 2 is preferably in a range of 136 mm to 166 mm.

In a case of the compact applicator, with a regular type tampon (manufactured by Uni-Charm Corporation) having the applicator 31 of 85 mm in total length, the length in the longitudinal direction of the bag body 2 is preferably in a range of 95 mm to 125 mm. With a super type tampon (manufactured by Uni-Charm Corporation) having the applicator 31 of 88 mm in total length, the length in the longitudinal direction of the bag body 2 is preferably in a range of 98 mm to 128 mm.

A width of the bag body 2 is preferably in a range of 180% to 320% of an outer diameter of the outer cylinder 34 of the applicator 31, and more preferably, about 270% thereof. More specifically, in a case of the long applicator, with a light type tampon (manufactured by Uni-Charm Corporation) having the outer cylinder 34 of 12.9 mm in outer diameter, the width of the bag body 2 is preferably in a range of 23 to 41 mm, and more preferably 29 mm. With a regular type tampon (manufactured by Uni-Charm Corporation) having the outer cylinder 34 of 13.4 mm in outer diameter, the width of the bag body 2 is preferably in a range of 24 to 43 mm, and more preferably 30 mm. With a super type tampon (manufactured by Uni-Charm Corporation) having the outer cylinder 34 of 16.4 mm in outer diameter, the width of the bag body 2 is preferably in a range of 30 to 52 mm, and more preferably 36 mm. With other products having the outer cylinder 34 of 17.6 mm in outer diameter, the width of the bag body 2 is preferably in a range of 23 to 56 mm, and more preferably 39 mm.

In a case of the compact applicator, with a regular type tampon (manufactured by Uni-Charm Corporation) having the outer cylinder 34 of 13.4 mm in outer diameter, the width of the bag body 2 is preferably in a range of 24 to 43 mm, and more preferably 30 mm. With a super type tampon (manufactured by Uni-Charm Corporation) having the outer cylinder 34 of 16 mm in outer diameter, the width of the bag body 2 is preferably in a range of 29 to 51 mm, and more preferably 36 mm.

An adhesion width in both end portions in the longitudinal direction of the bag body 2 is preferably in a range of 3 to 6 mm.

A distance between the first lateral joint portion 23 and the second lateral joint portion 24 in the bag body 2 is preferably in a range of 10 to 40 mm in order to form the slack portion 28 in the bag body 2, thereby forming a superior oval-shaped cross-section in the width direction thereof.

In a case of the long applicator, with a light type tampon (manufactured by Uni-Charm Corporation) having the bag body 2 of 155 to 185 mm in total length, a length in the longitudinal direction of the flap portion 5 is, specifically, in a range of 20 to 104 mm. With a regular type tampon (manufactured by Uni-Charm Corporation) having the bag body 2 of 127 to 157 mm in total length, the length in the longitudinal direction of the flap portion 5 is in a range of 20 to 107 mm. With a super type tampon (manufactured by Uni-Charm Corporation) having the bag body 2 of 130 to 160 mm in total length, the length in the longitudinal direction of the flap portion 5 is in a range of 20 to 109 mm. With other products having the bag body 2 of 136 to 166 mm in total length, the length in the longitudinal direction of the flap portion 5 is in a range of 80 to 115 mm.

In a case of the compact applicator, with a regular type tampon (manufactured by Uni-Charm Corporation) having the bag body 2 of 95 to 115 mm in total length, the length in the longitudinal direction of the flap portion 5 is preferably in a range of 20 mm to 81.5 mm. With a super type tampon (manufactured by Uni-Charm Corporation) having the bag body of 98 to 118 mm in total length, the length in the longitudinal direction of the flap portion 5 is preferably in a range of 20 to 84 mm.

A length in the longitudinal direction of the grip portion 6 in the flap portion 5 is preferably in a range of 5 to 20 mm.

According to the individual packaging body of a tampon 1 in the present embodiment thus configured, as shown in FIG. 5, by providing the slack portion 28 in the flat bag body 2, in the bag body 2 from which a tampon is taken out for use, the first face 21 and the second face 22 do not closely contact each other and are spaced apart from each other, thereby forming a gap therebetween. This facilitates insertion of the used applicator 31 into the bag body 2 and inhibits soiling of an outer face side of the bag body 2 at the time of insertion. As a result, the bag body 2 can be kept clean even after inserting the applicator 31. Furthermore, at the time of using the tampon, there is also an effect of facilitating removal of the tampon from the bag body 2.

In addition, since the first lateral joint portion 23, the second lateral joint portion 24, and the bottom joint portion 26 are joined by heat sealing, in the individual packaging body of a tampon 1 in the present embodiment, a substantially oval shaped torn opening can be easily formed when the tampon is being taken out therefrom. As a result, a user can easily open the torn opening with one hand when inserting the used applicator 31 into the bag body 2, thereby further facilitating insertion of the used applicator 31 into the bag body 2.

Next, a manufacturing method of the individual packaging body of a tampon of the present invention is described hereinafter based on a preferred embodiment, with reference to FIGS. 7 and 8.

Figure 7:
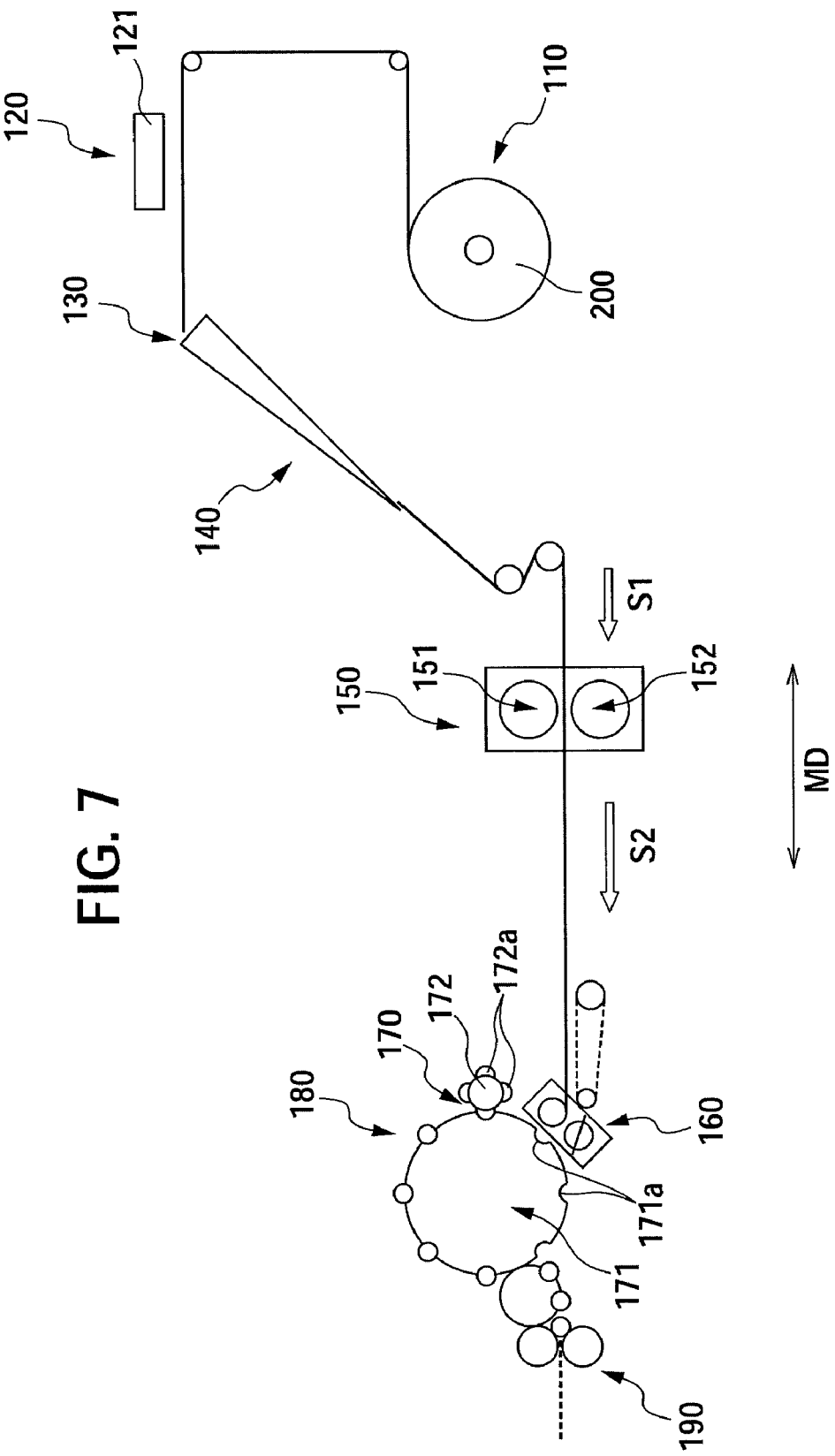
FIG. 7 is a schematic view illustrating manufacturing steps of the individual packaging body of a tampon of the present embodiment.

According to the present embodiment of a manufacturing method of the individual packaging body of a tampon 1, the individual packaging body of a tampon has an elongated and flat bag body configured with a sheet-like member and a tampon with an applicator that is to be individually packed in the bag body, and the method includes: an unreeling step 110 of unreeling a strip-shaped sheet-like member 200 from a raw fabric as shown in FIG. 7; a folding step 140 of folding the strip-shaped sheet-like member 200 so that both end portions in a CD direction, which is orthogonal to a flow direction of the strip-shaped sheet-like member (MD direction), overlap each other; a bag body continuous body forming step 150 of forming a bag body continuous body having a one end in the CD direction being an open end, by way of joining by heat sealing in the CD direction, at predetermined intervals in the MD direction, in a state that the strip-shaped sheet-like member 200 is extended in the MD direction; an insertion step 180 of inserting the tampon into the bag body continuous body from the open end; and a joining step 190 of joining the open end by heat sealing.

More specifically, the manufacturing method of the individual packaging body of a tampon 1 of the present embodiment includes the following steps (a) to (i).

(a) Unreeling step 110
(b) Slit forming step 120
(c) Grip portion forming step 130
(d) Folding step 140
(e) Bag body continuous body forming step 150
(f) Cutting step 160
(g) Opening step 170
(h) Inserting step 180
(i) Joining step 190

The manufacturing method of the present invention manufactures an individual packaging body of a tampon 1 including an elongated and flat bag body 2 configured with a sheet-like member and a tampon with an applicator 3 that is to be individually packed in the bag body 2.

(a) In the unreeling step 110, a strip-shaped sheet-like member 200 is unreeled from a raw fabric, which is rolled on a drum or the like, in a predetermined direction at a predetermined rate. For example, the strip-shaped sheet-like member 200 is supplied in a state as shown in (A) in FIG. 8. The strip-shaped sheet-like member 200 may include a strip-shaped sheet-like member 200 having the rear surface or the front surface applied with the embossing process. In this case, an embossing process step (not shown) may be provided.

(b) In the slit forming step 120 (see FIG. 7) a slit portion 41 as shown in (B) in FIG. 8, is formed for example, by a slit portion forming means 121 such as a predetermined laser device, at a predetermined position on the strip-shaped sheet-like member 200 so that the bag body 2 can be cut off. Not only the laser device, but also a device with a rotary cutter with a blade of a perforated line can be used as the slit portion forming means 121.

(c) In the grip portion forming step 130 (see FIG. 7) a grip portion 6 as shown in (C) in FIG. 8, is formed by folding the strip-shaped sheet-like member 200 into a sail-shape. More specifically, the strip-shaped sheet-like member 200 is folded down into the rear surface side at a valley portion 202a thereof. Then, the strip-shaped sheet-like member 200 is folded down into the surface side at a peak portion 202b thereof. By thus folding down the valley portion 202a and the peak portion 202b in predetermined directions respectively, the grip portion 6 is formed. A fold in the valley portion 202a and the peak portion 202b of the strip-shaped sheet-like member 200 can be, for example, formed by placing an edge portion of a steel plate and the like on the strip-shaped sheet-like member 200 (not shown).

(d) In the folding step 140 (see FIG. 7) the strip-shaped sheet-like member 200 on which the grip portion 6 is formed in the grip portion forming step 130, is further folded into two toward a surface side as shown in (D) in FIG. 8. As a result, the strip-shaped sheet-like member 200 is shaped into a substantially flat shape in which the first face 21 and the second face 22 face each other and the grip portion 6 is provided on the first face 21 side.

(e) In the bag body continuous body forming step 150 (see FIG. 7), a bag body continuous body 210 is formed to have one end in the longitudinal direction (CD direction) being an open end 208, by way of joining by heat sealing extending in the longitudinal direction (CD direction), at predetermined intervals in the flow direction (MD direction), in a state that the strip-shaped sheet-like member 200 is extended in the flow direction (MD direction) as shown in (E) in FIG. 8. More specifically, first, the strip-shaped sheet-like member 200 is joined from a lower end portion in the MD direction to a position where the slit portion 41 is formed. Subsequently, both sides of the flap portion 5 in the longitudinal direction are joined. In this case, the flap portion 5 is joined so as to be detachable. The first lateral joint portion 23 and the second lateral joint portion 24 are formed by the abovementioned joining by heat sealing.

The strip-shaped sheet-like member 200 can be expanded in the flow direction by, for example, changing a conveying speed of the strip-shaped sheet-like member 200 before and after the bag body continuous body forming step 150. In other words, the strip-shaped sheet-like member 200 can be expanded by making a conveying speed S2 of the strip-shaped sheet-like member 200 after the bag body continuous body forming step 150 (see FIG. 7) faster than a conveying speed S1 of the strip-shaped sheet-like member 200 before the bag body continuous body forming step 150 (see FIG. 7). The ratio of the speed before and after the bag body continuous body forming step 150 (S2/S1) is preferably in a range of 1.01 to 1.05.

Joining by heat sealing can be performed by, for example, heating an upper rotary metal roller 151 and a lower rotary metal roller 152 and sandwiching the strip-shaped sheet-like member 200 by the two rotary metal rolls 151 and 152 that are heated, as shown in FIG. 7. The metal roller can be either a planar roller or an embossing roller. In the present embodiment, a heat sealing process is performed by using a combination of a planar roller and an embossing roller having a plurality of convex portions of a predetermined shape on a peripheral surface thereof, disposing the planar roller on the second face 22 side and the embossing roller on the first face 21 side.

(f) In the cutting step 160 (see FIG. 7), as shown in (F) in FIG. 8, the bag body continuous body 210 having an open end 208 at one end is cut at a predetermined position 206 at predetermined intervals, so as to form the bag body 2 having the open end 208 at the end. For example, a rotary cutter can be used as a cutting means.

(g) In the opening step 170, the open end 208 of the bag body 2 having an end being the open end 208 is opened and kept an opening shape thereof, by a suction drum 171 and an opening convex drum 172 as shown in FIG. 7. In the opening step 170, the bag body 2 having an end being the open end 208 is transferred to the suction drum 171. The suction drum 171 has a large number of substantially semicircular concave portions 171*a* provided on a peripheral surface thereof and a plurality of suction holes (not shown) in a bottom portion of the substantially semicircular concave portions 171*a* and in the vicinity of a border between the substantially semicircular concave portions 171*a* and the peripheral surface of the drum. The transferred bag body 2 having the end being the open end 208 is held at the substantially semicircular concave portions 171*a* of the suction drum 171 at a predetermined position, by suctioning air from the suction hole. The opening convex drum 172 is disposed so as to face the suction drum 171 and has a plurality of substantially semicircular convex portions 172*a* that is substantially similar in size to the substantially semicircular concave portions 171*a* provided on the suction drum 171. In addition, a suction hole (not shown) is provided in the vicinity of an apex portion of the substantially semicircular shaped convex portions 172*a*. As the bag body 2 having the end being the open end 208 that is held on the suction drum 171 passes through the opening convex drum 172, the convex portion 172*a* of the opening convex drum 172 enters the concave portion 171*a* of the suction drum 171, and the bag body 2 is opened by way of suction by the suction hole provided in the vicinity of the apex portion of the convex portion 172*a* and conveyed to an inserting step 180 in a state of being open.

(h) In the inserting step 180 (see FIG. 7) the tampon with an applicator 3 is inserted into the bag body 2 with the end being the open end 208, which is opened, as shown in (G) in FIG. 8. In this case, the tampon with an applicator 3 is inserted from a direction of the inner cylinder 45 of the applicator 31, in other words from a side of the string 33. The tampon with an applicator 3 is inserted into a bag body 2 with the end being the open end 208 by introducing a tampon insertion nozzle (not shown) into the open end 208 that is opened in the opening step 170, and then inserting the tampon from the tampon insertion nozzle.

(i) In the joining step 190 (see FIG. 7) the open end 208 of the bag body 2 with the end being the open end 208 is joined, into which the tampon with an applicator 3 is inserted, thereby packing the tampon with an applicator 3 as shown in (H) in FIG. 8. The individual packaging body of a tampon 1 is thus completed. As a joining means, heat sealing by a rotary roller having a lattice pattern, a corrugating sealing process and the like can be exemplified.

According to the manufacturing method of the individual packaging body of a tampon 1 of the present invention including the abovementioned steps, the individual packaging body of a tampon 1 of the present invention having a slack portion 28 in the bag body 2 can be easily manufactured.

In addition, the slack portion 28 can be easily formed by way of joining by heat sealing the strip-shaped sheet-like member 200 in an expanded state in the flow direction at predetermined intervals, and forms the first lateral joint portion 23 and the second lateral joint portion 24, since the sheet-like member shrinks from the expanded state and heat-shrinks due to heat sealing.

Furthermore, by providing the opening step 170, the tampon with an applicator 3 can be infallibly inserted into the bag body 2, which is formed in a flat shape, in the inserting step 180.

In addition, in the inserting step 180, by inserting the tampon with an applicator 3 from a side of the string 33 into the bag body 2 with three sides closed, entanglement of the string 33 can be avoided in the joining step 190 of joining the open end 208.

Furthermore, in the manufacturing method in the present embodiment, since the individual packaging body of a tampon 1 can be manufactured in a lateral flow, the tampon with an applicator 3 packed in the bag body 2 is stably positioned and the petals 36 of the applicator 31 are not easily damaged by heat for joining in the joining step 190.

The present invention has been described based on a preferred embodiment and a preferred aspect; however, the present invention is not limited thereto and modifications can be made accordingly within the technical scope of the present invention.

The slack portion 28 can also be formed by changing a width of the sheet-like member constituting the first face 21 from a width of the sheet-like member constituting the second face 22. In addition, the slack portion 28 can be formed only on any one of the first face 21 and the second face 22.

A shape of the tearing portion 4 is not limited to the mountain shape and can be a semicircular shape that curves to project toward the folded end 27 or the bottom portion 25, a wave shape, or a linear shape.

In addition, in the present embodiment, a heat sealing process in the bag body continuous body forming step 150 is performed by a combination of a planar roller and an embossing roller having a plurality of convex portions of a predetermined shape on a peripheral surface thereof; however, the heat sealing process can be performed by a combination of two embossing rollers each having a plurality of convex portions of a predetermined shape on a peripheral surface thereof.

In a case where the heat sealing process is performed by a combination of a planar roller and an embossing roller having a plurality of convex portions of a predetermined shape on a peripheral surface thereof, a region on the second face 22, which is contacted by the planar roller, in the vicinity of the first lateral joint portion 23 and the second lateral joint portion 24 is affected by heat more than a region on the first face 21, which is contacted by the embossing roller, in the vicinity of the first lateral joint portion 23 and the second lateral joint portion 24. Therefore, the bag body 2 in which a length between the first lateral joint portion 23 and the second lateral joint portion 24 on the first face 21 is different from a length between the first lateral joint portion 23 and the second lateral joint portion 24 on the second face 22, due to a difference in the effect of heat thereon, is formed.

On the other hand, in a case where the heat sealing process is performed using a combination of two embossing rollers each having a plurality of convex portions of a predetermined shape on a peripheral surface thereof, heat is applied equally to the first face 21 and the second face 22. Therefore, a length between the first lateral joint portion 23 and the second lateral joint portion 24 on the first face 21 and a length between the first lateral joint portion 23 and the second lateral joint portion 24 on the second face 22 does not differ due to the heat sealing process.

Furthermore, in the bag body continuous body forming step 150 of the present embodiment, the first lateral joint portion 23 and the second lateral joint portion 24 are formed by a 2-step process of firstly joining the strip-shaped sheet-like member 200 from a lower end portion to a position where the slit portion 41 is formed in the CD direction, and then joining both end portions of the flap portion 5 in the longitudinal direction; however, the first lateral joint portion 23 and the second lateral joint portion 24 can be formed by joining a region between both end portions in the CD direction at once. In this case, it is preferable to change the seal strength by changing a joining pattern of heat sealing between the flap portion 4 and other portion.

The invention claimed is:

1. An individual packaging body of a tampon comprising:
   an elongated and flat bag body configured with a sheet-like member; and
   a tampon with an applicator that is to be individually packed in the bag body, wherein
   the bag body comprises:
   a first face and a second face that configure the bag body and are disposed so as to face each other;
   a first lateral joint portion and a second lateral joint portion that join the first face and the second face on two sides in a width direction;
   a tearing portion disposed near one end in a longitudinal direction of the bag body, the tearing portion having at least one slit portion that is formed continuously or intermittently so as to extend in the width direction of the bag body;
   a bottom joint portion that is formed in a bottom portion, which is at the other end in the longitudinal direction, so as to connect the first lateral joint portion and the second lateral joint portion, and joins the first face and the second face;
   a slack portion that is formed on at least one of the first face and the second face, and configured so that a length of the sheet-like member between the first lateral joint portion and the second lateral joint portion on the at least one of the first face and the second face is greater than a distance between the first lateral joint portion and the second lateral joint portion,
   wherein the slack portion slackens more greatly on a side of the other end of the bag body than in the side of the one end, and the slack portion is formed of the sheet-like member without being folded.

2. The individual packaging body of a tampon according to claim 1, wherein the bag body includes:
   a flap portion that is openable by a force in the longitudinal direction of the bag body, and
   wherein the tearing portion is disposed on the first face at a position a predetermined distance away from the one end opposing to the bottom joint portion.

3. The individual packaging body of a tampon according to claim 1,
   wherein the bag body is configured so that, in an open state, a length in the longitudinal direction of the second face is greater than a length in the longitudinal direction of the first face.

4. The individual packaging body of a tampon according to claim 1,
   wherein a width of the first face and the second face is the same, and
   wherein a distance in the bag body between the first lateral joint portion and the second lateral joint portion in the tearing portion is greater than a distance between the first lateral joint portion and the second lateral joint portion in the bottom portion.

5. The individual packaging body of a tampon according to claim 1,
   wherein the sheet-like member is configured with a film material, and the first lateral joint portion, the second lateral joint portion, and the bottom joint portion are joined by heat sealing.

6. An individual packaging body of a tampon comprising:
   an elongated and flat bag body configured with a sheet-like member; and
   a tampon with an applicator that is to be individually packed in the bag body, wherein
   the bag body comprises:
   a first face and a second face that configure the bag body and are disposed so as to face each other;
   a first lateral joint portion and a second lateral joint portion that join the first face and the second face on two sides in a width direction;
   a tearing portion disposed near one end in a longitudinal direction of the bag body; and
   a bottom joint portion that is formed in a bottom portion, which is at the other end in the longitudinal direction, so as to connect the first lateral joint portion and the second lateral joint portion, and joins the first face and the second face,
   wherein, in a case where the bag body is in a natural state, the first face and the second face each have a non-flat portion and in the non-flat portion, the first face and the second face are spaced away from each other and a gap is formed between the first face and the second face, and the gap is formed more greatly on a side of the other end of the bag body than in the side of the one end, and
   the non-flat portion is formed of the sheet-like member without being folded.

7. The individual packaging body of a tampon according to claim 1, wherein a petal portion of the tampon is positioned in the slack portion in a state that the tampon is housed in the packaging body.

8. The individual packaging body of a tampon according to claim 1, wherein, in a state in which the tearing portion is torn, a portion of a transverse edge of the torn first face protrudes in a direction away from the bottom joint portion.

* * * * *

UNITED STATES PATENT AND TRADEMARK OFFICE
CERTIFICATE OF CORRECTION

PATENT NO. : 8,286,793 B2
APPLICATION NO. : 12/595157
DATED : October 16, 2012
INVENTOR(S) : Kondo et al.

Page 1 of 1

It is certified that error appears in the above-identified patent and that said Letters Patent is hereby corrected as shown below:

<u>On the Title Page</u>

Item [22], the PCT Filed date, delete "November 4, 2008" and insert --April 11, 2008-- in its place.

Signed and Sealed this
Tenth Day of September, 2013

Teresa Stanek Rea
*Acting Director of the United States Patent and Trademark Office*